(12) United States Patent
Sei et al.

(10) Patent No.: US 7,538,137 B2
(45) Date of Patent: May 26, 2009

(54) 1-O-β-D-GLUCOPYRANOSYLGERANIOL-10,5-OLIDE AND USE THEREOF

(75) Inventors: Yasuo Sei, Tokyo (JP); Yoshihiro Kano, Tokyo (JP); Ryotarou Takabori, Tokyo (JP)

(73) Assignee: Iskra Industry Co., Ltd., Tokyo (JP)

( * ) Notice: Subject to any disclaimer, the term of this patent is extended or adjusted under 35 U.S.C. 154(b) by 425 days.

(21) Appl. No.: 11/437,769

(22) Filed: May 22, 2006

(65) Prior Publication Data

US 2007/0059339 A1 Mar. 15, 2007

(30) Foreign Application Priority Data

Sep. 13, 2005 (JP) ............................. 2005-265430

(51) Int. Cl.
- *A01N 43/16* (2006.01)
- *A61K 31/35* (2006.01)
- *A01N 43/08* (2006.01)
- *A61K 31/34* (2006.01)
- *A61K 47/00* (2006.01)

(52) U.S. Cl. ..................... 514/456; 514/470; 424/439
(58) Field of Classification Search ............... 514/456, 514/470; 424/439
See application file for complete search history.

(56) References Cited

FOREIGN PATENT DOCUMENTS

JP 2001-2579 1/2001

*Primary Examiner*—Yong S Chong
(74) *Attorney, Agent, or Firm*—Nixon & Vanderhye, PC

(57) ABSTRACT

A novel natural compound having various therapeutically effects is provided. The compound is obtainable from *Sibiraea* leaves by aqueous extraction and is represented by a formula (1) as follows.

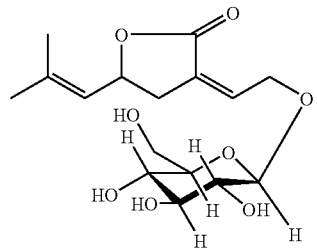

(1)

9 Claims, 6 Drawing Sheets $^1$H-NMR : 500MHz (C$_5$D$_5$N)

$^{13}$C-NMR : 125MHz (C$_5$D$_5$N)

Mass spectrum: SIMS (posi), glycerol

| NO. | m/z | INT. | INT% |
|---|---|---|---|
| 7 | 42 | 25,935 | 22.1 |
| 13 | 54 | 34,827 | 29.7 |
| 15 | 56 | 27,908 | 23.8 |
| 25 | 70 | 27,029 | 23.0 |
| 30 | 79 | 26,642 | 22.7 |
| 32 | 81 | 40,624 | 34.6 |
| 34 | 83 | 38,229 | 32.6 |
| 36 | 85 | 40,649 | 34.6 |
| 40 | 91 | 26,393 | 22.5 |
| 65 | 119 | 35,112 | 29.9 |
| 69 | 123 | 43,041 | 36.7 |
| 107 | 165 | 117,360 | 100.0 |
| 122 | 183 | 73,500 | 62.6 |
| 215 | 345 | 2,183 | 1.9 |

¹H-NMR spectrum

¹H-NMR spectra tocsy noesy ghsqcs ghmbc

1-O-β-D-GLUCOPYRANOSYLGERANIOL-10,5-OLIDE AND USE THEREOF

CROSS-REFERENCE TO RELATED APPLICATIONS

This application is based upon and claims the benefit of priority from prior Japanese Patent Application No. 2005-265430, filed on Sep. 13, 2005, the entire contents of which are incorporated herein by reference.

BACKGROUND OF THE INVENTION

The present invention relates to 1-O-β-D-glucopyranosylgeranio-10,5-olide and a use thereof.

Adipositas is medically defined as pathology complicating health disorders resulting from obesity or giving a prospect of clinical complications thereof, and medically requiring weight loss. Obesity is physiologically a condition of excess accumulation of adipose tissue in the body. Obesity can be quantitatively judged by body mass index (BMI). For example, BMI over 25 enhances onset frequency of arteriosclerosis such as atherosclerosis, and its complications. High BMI, that is, obesity is believed to be a risk factor for angina pectoris and myocardial infarction.

An example of obesity ameliorating agents accepted by Japan (Ministry of Health, Labor and Welfare) is mazindol. Use of mazindol is highly limited. For example, mazindol is limited to use for grave patients such as those having a BMI of 35 or more, and its use period is limited to 3 months or shorter. Obesity ameliorating agents that have few use limitation are desired.

Hyperlipemia is defined as a symptom in which lipids in blood, particularly cholesterol, shows high concentration over the normal value, and clinically known as icteric diseases such as cholecystolithiasis, acute pancreatitis, yellow nail and the like. Hyperlipemia enhances onset frequency of arteriosclerosis such as atherosclerosis. Hyperlipemia is a risk factor for angina pectoris and myocardial infarction. Examples of clinically utilizable lipid metabolism ameliorating agents include clofibrate, nicotinic acid derivatives, hydroxymethylglutaryl CoA (HMG-CoA) reductase inhibitor (statin-type drug formulation), protein anabolized steroid, plant sterol.

Hyperglycemia is a factor causing capillaropathy such as nephropathy, retinopathy and the like; peripheral blood vessel injury, dysautonomia, renal insufficiency and blindness. Duration of hyperglycemia is known as diabetes. Diabetes requires periodic dialysis treatment. Diabetes remarkably lowers the quality of life (QOL). Hyperglycemia promotes arteriosclerosis and is a risk factor for angina pectoris and myocardial infarction. Examples of clinically utilizable hypoglycemic agents include glibenclamide, sulfonylurea-based drug formulations, α-glucosidase inhibitors, insulin resistance ameliorating agents and biguanide agents.

One cause for alopecia is blood circulation disorder. Examples of causes for alopecia include blood circulation disorder around hair follicle ascribable to biased nutrition and irregular life, blood circulation disorders of the scalp ascribable to stress, heredity, androgen, use of hear removers and hair dyeing agents, smoking and alcohol drinking. Examples of clinically utilizable hair growth ameliorating agents include adrenocortical hormones, carpronium chloride, minoxidil and capsaicin.

Japanese Patent Laid-Open Publication No. 2001-2579 discloses a lipid metabolism controlling agent containing leaves of *Sibiraea angustata* (Rchd.) Hand. Mazz., or *Sibiraea* leave(s). This lipid metabolism controlling agent lowers plasma triacylglycerol concentration and increases free fatty acid concentration. This lipid metabolism controlling agent can be used as a medicinal drug formulation, food or feed. This lipid metabolism controlling agent can be used for treatment or prophylaxis of diseases influencing lipid metabolism such as hypolipoproteinemia, hyperlipoproteinemia, diabetes, hypertriacylglycerolemia, hypercholesterolemia, arteriosclerosis and obesity. This lipid metabolism controlling agent is an aqueous extract of *Sibiraea* leaves.

SUMMARY OF THE INVENTION

*S. angustata* is distributed in bush flora and gravel areas at altitudes of 3000 to 4000 m in Qinghai, Gansu, Sichuan and Yunnan in China. *Sibiraea* leaves are Tibet folk medicine for treatment of maldigestion and, they say that when had it frequently, the body becomes healthy and when fed it to a domestic animal, the animal loses weight. *Sibiraea* leaves contain compounds such as lupin acid, lupinates, 2-hydroxyurson, urson, oleanolic acid, ferulic acid, Senpika esters and the like.

The inventors have examined various plant components, and a novel compound having an obesity ameliorating action, a lipid metabolism ameliorating action, a hypoglycemic action and a hair growth ameliorating action and have determined its structure.

One aspect of the present invention is a compound represented by a formula (1) as follows or a salt thereof.

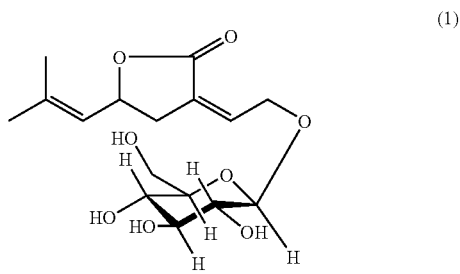

(1)

In one embodiment, the compound (1) can be contained in, for example, an obesity ameliorating agent, a lipid metabolism ameliorating agent, a hypoglycemic agent, a hair growth ameliorating agent, a healthy food, and a food, as an active ingredient.

Another aspect of the present invention is a method for producing a drug formulation comprising the compound (1). The method includes extracting leaves of *S. angustata* with a solvent, isolating the compound (1) from the extract, purifying the compound (1), and mixing a therapeutically effective amount of the compound (1) with a pharmaceutically acceptable carrier.

The present invention further provides a method for treating at least one of adipositas, hyperlipemia, diabetes, and alopecia in a patient. The method includes administering to the patient a therapeutically effective amount of the compound (1).

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF PREFERRED EMBODIMENTS

Figure 1A:
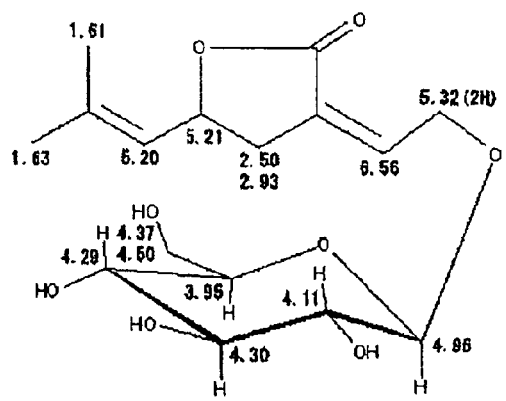
FIG. 1A shows a structure of the compound (I) appended with a value of $^1$H-NMR.
Figure 1B:
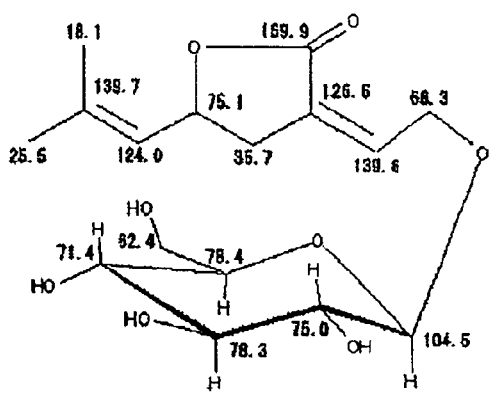
FIG. 1B shows a structure of the compound (I) appended with a value of $^{13}$C-NMR.
Figure 2:
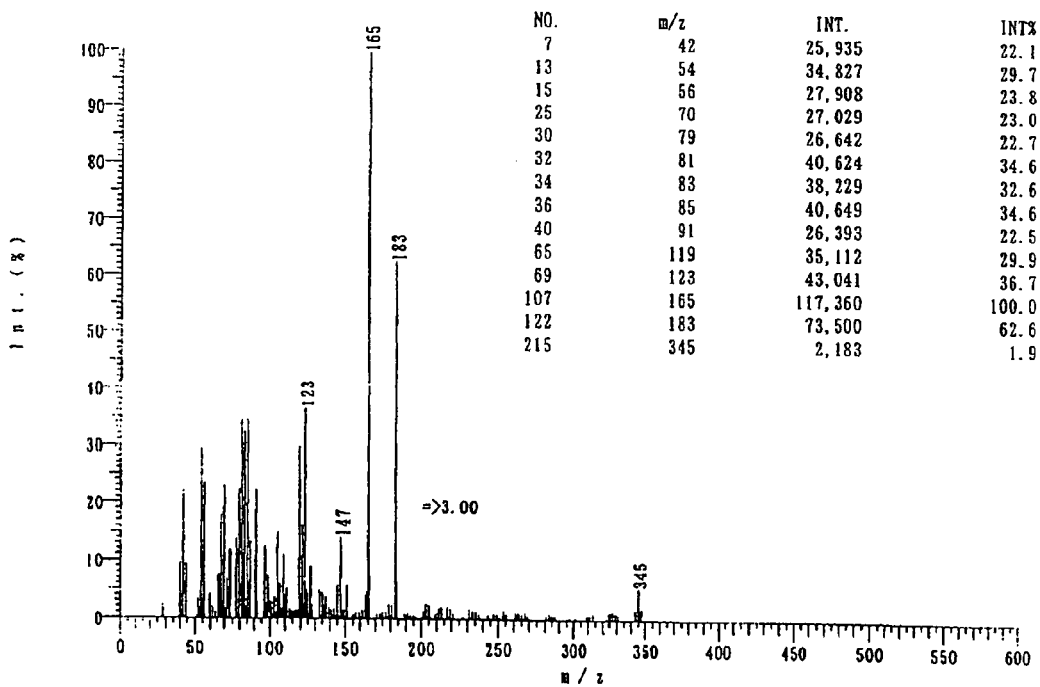
FIG. 2 shows a mass spectrum of the compound (I)
Figure 3:
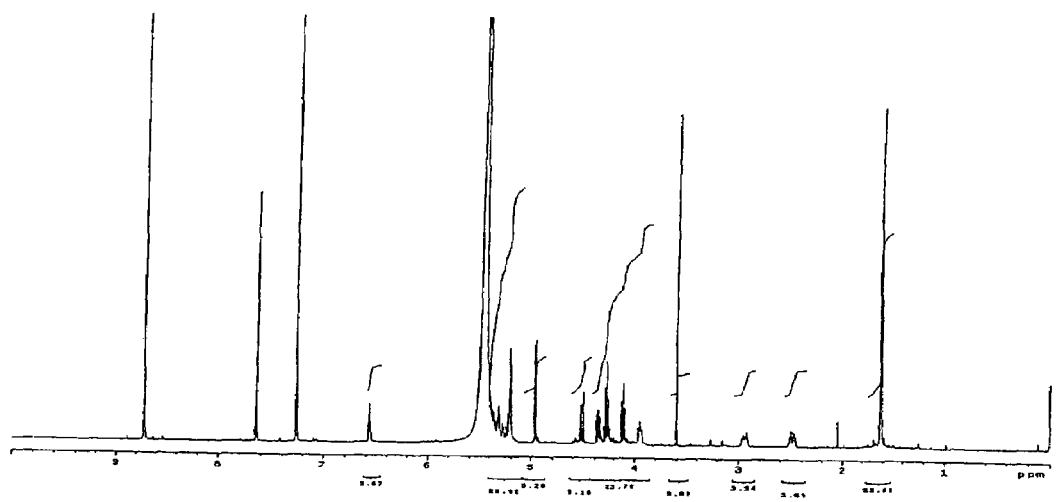
FIG. 3 shows a $^1$H-NMR spectrum of the compound (I)
Figure 4:
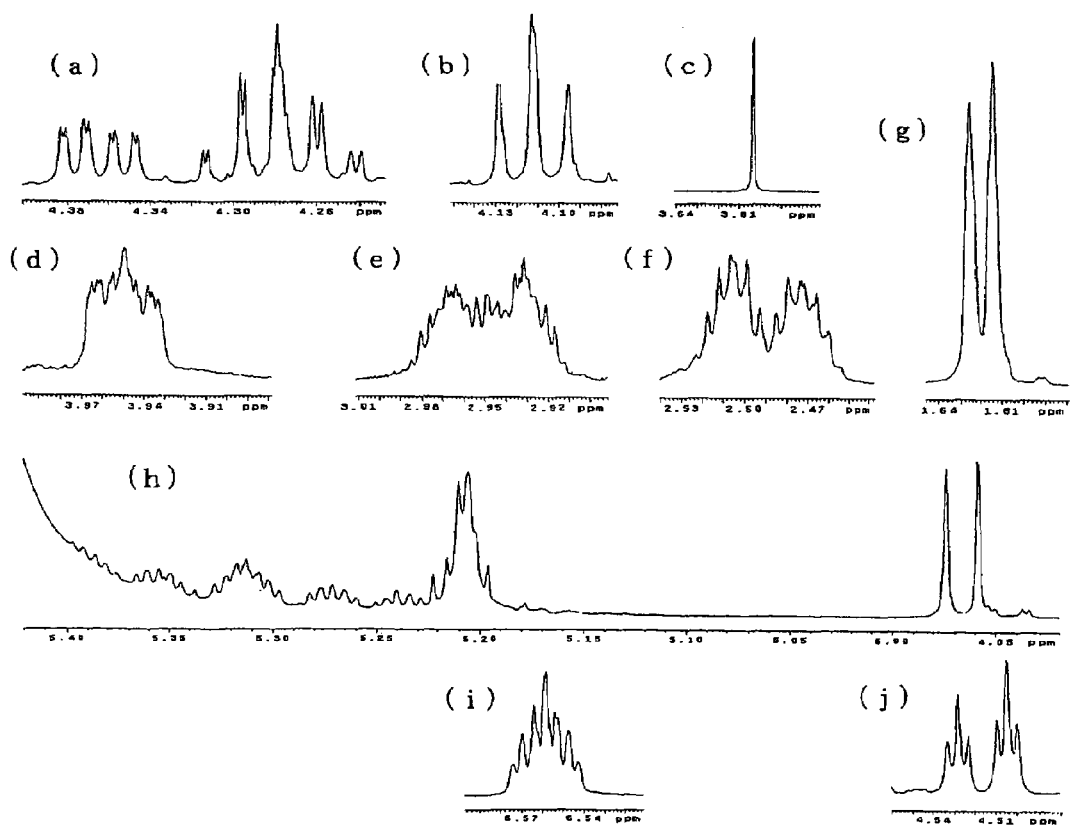
FIG. 4 shows partially enlarged views of the $^1$H-NMR spectrum of FIG. 3.
Figure 5:
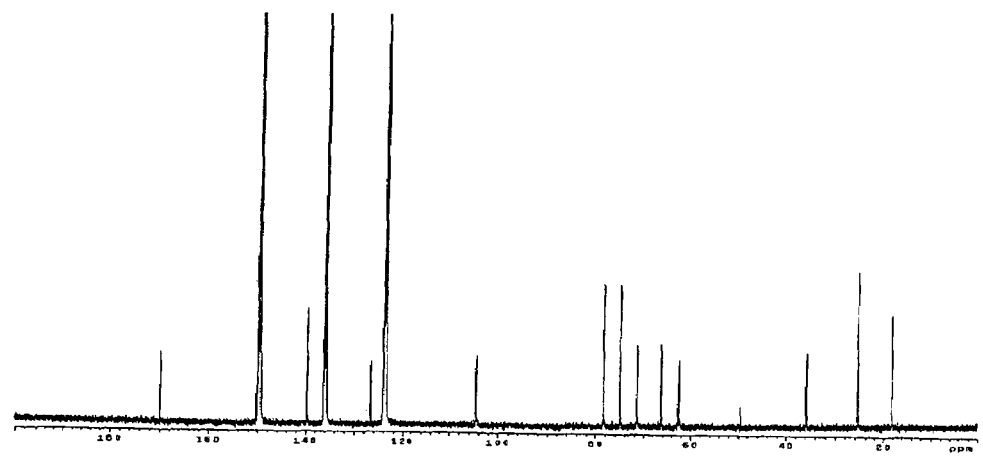
FIG. 5 shows a $^{13}$C-NMR spectrum of the compound (I)
Figure 6A:
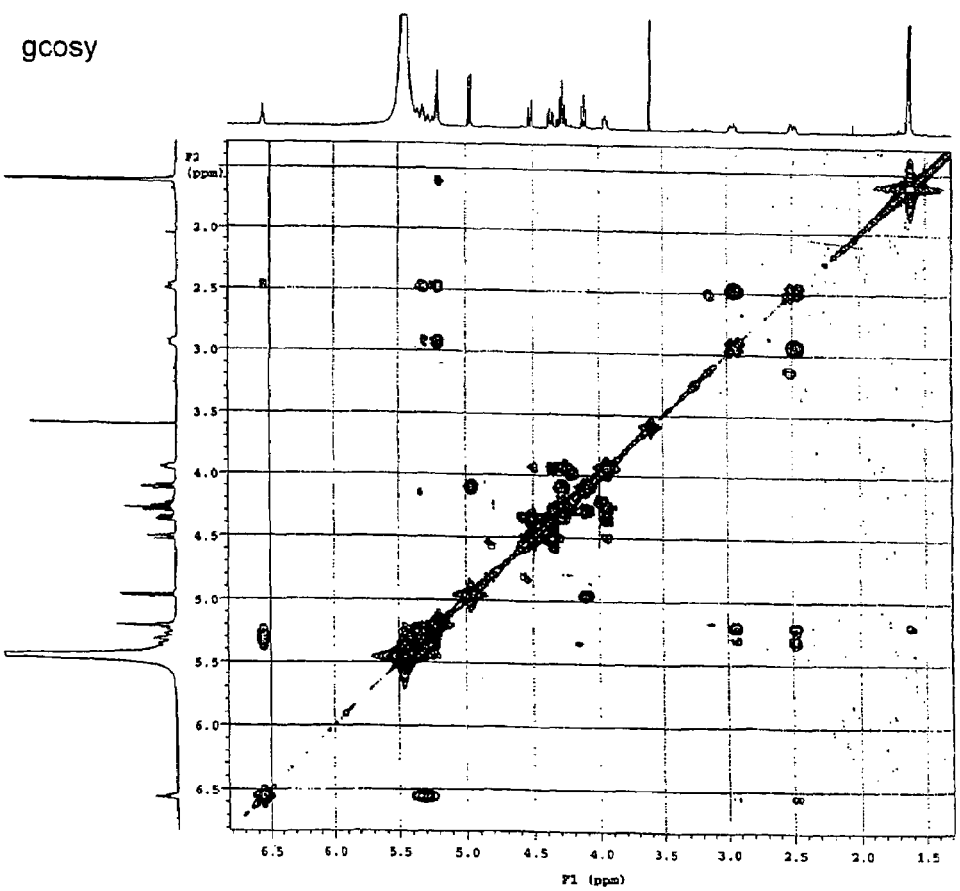
FIGS. 6A, B and C show a homo-nuclide two-dimensional NMR spectrum of the compound (I)
Figure 6B:
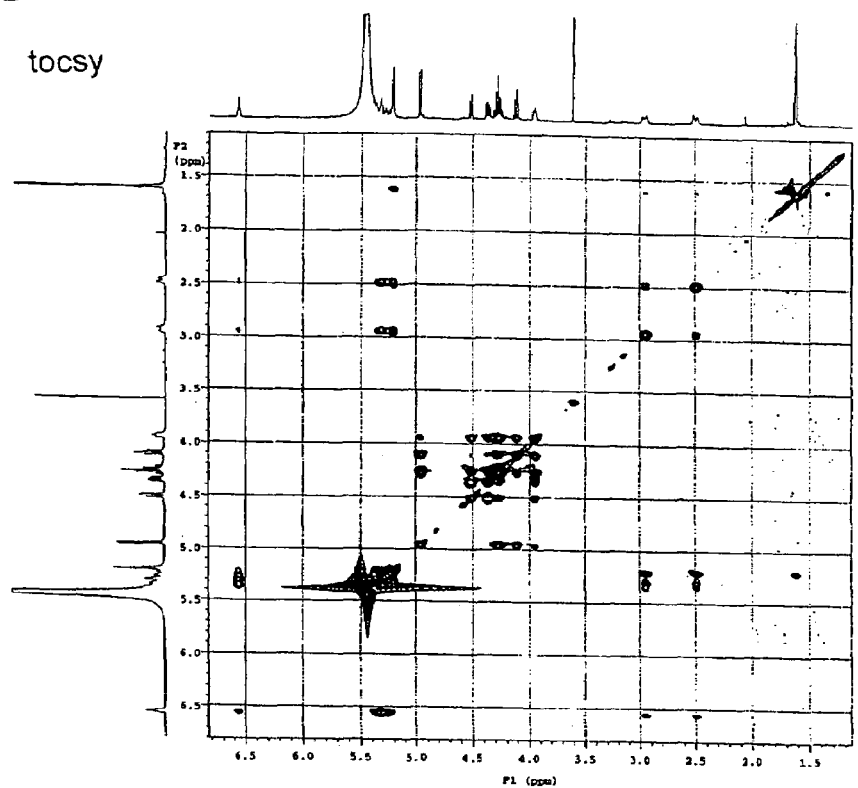
Figure 6C:
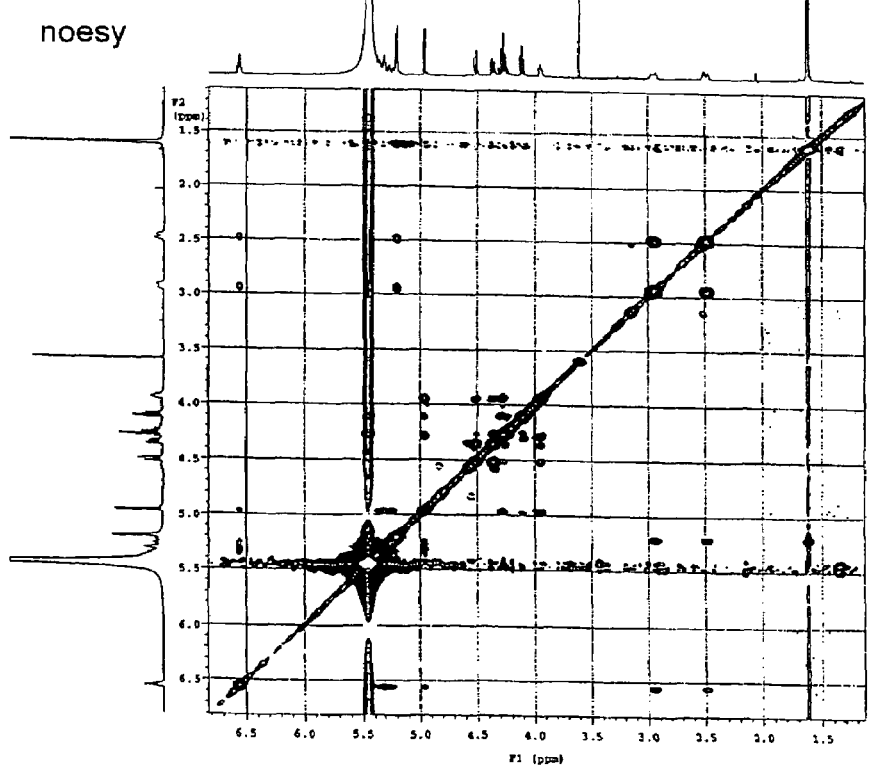
Figure 7A:
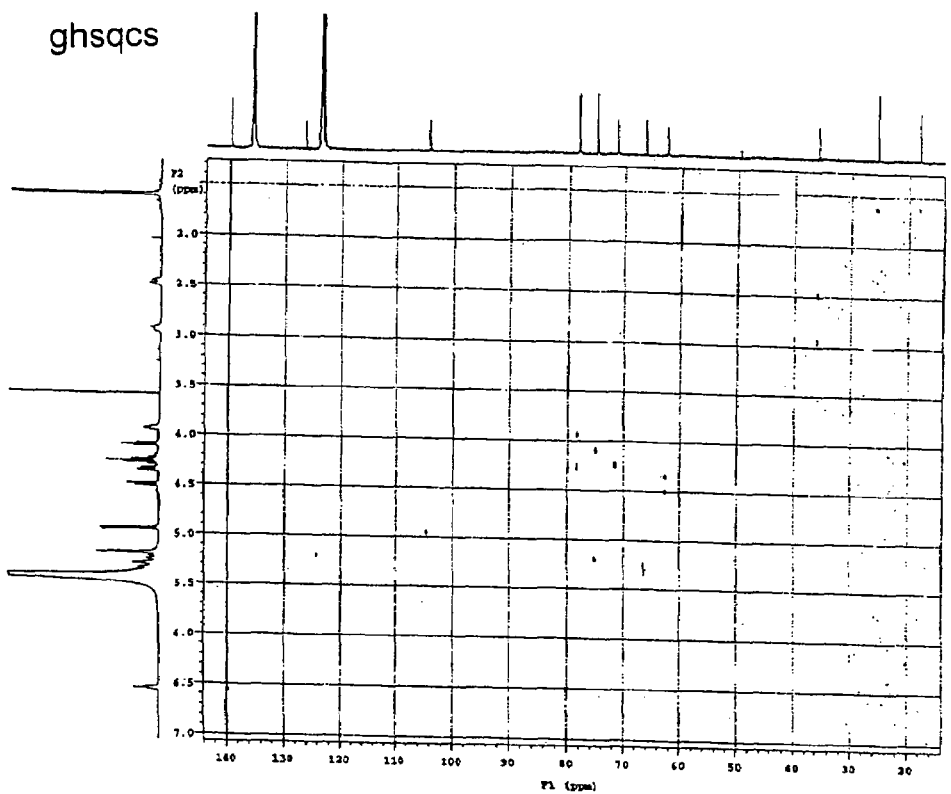
FIGS. 7A and B show hetero-nuclide two-dimensional NMR spectra of the compound (I), respectively.
Figure 7B:
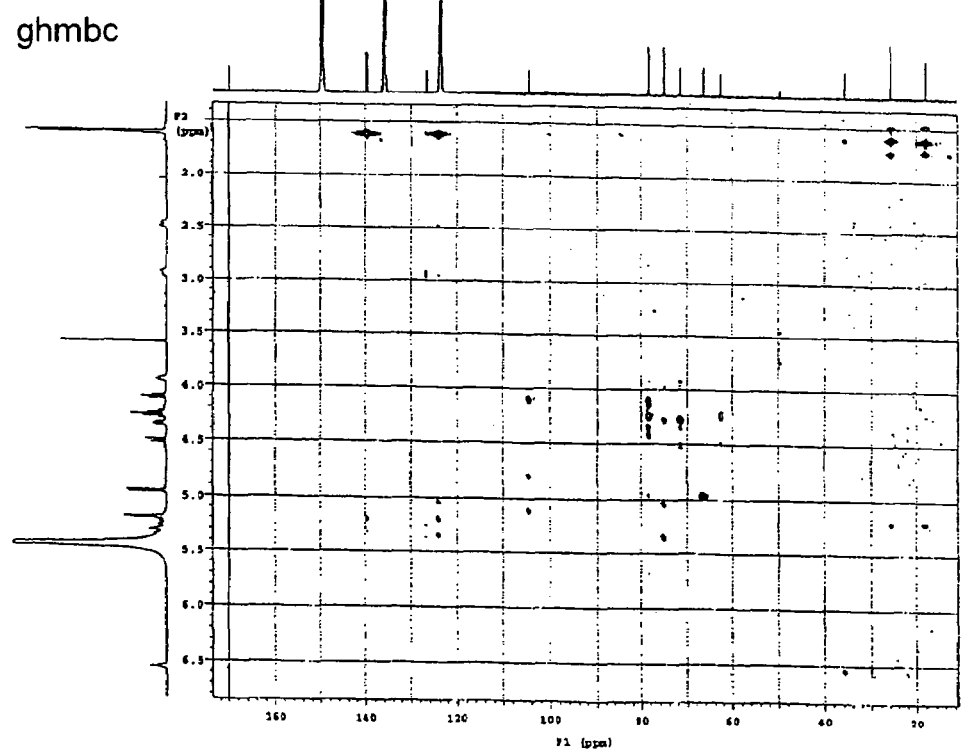

One embodiment specifically describing the compound, the obesity ameliorating agent, the lipid metabolism ameliorating agent, the hypoglycemic agent and the hair growth ameliorating agent of the present invention will be illustrated below.

The compound of this embodiment (hereinafter, referred to as compound (I)) is represented by the formula (1).

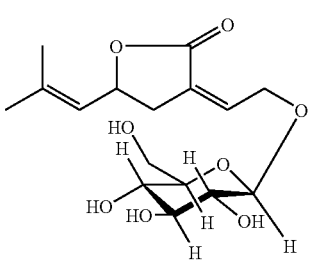

(1)

The compound (I) has a molecular weight of 344 and is represented by the molecular formula: $C_{16}H_{24}O_8$, and its name according to the nomenclature of IUPAC is 1-O-β-D-glucopyranosylgeraniol-10,5-olide.

The compound (I) is contained in a crude drug obtained by processing leaves of S. angustata.

The compound (I) is obtainable by, for example, extracting leaves of S. angustata with water, lower alcohol or water-containing lower alcohol and purifying its extract. Examples of the lower alcohol include methanol, ethanol, butanol, propanol and isopropanol. The water-containing lower alcohol preferably contains lower alcohol in a proportion of 50% or more, more preferably 80% or more.

When the above-mentioned extract is purified, known chromatography carriers such as activated carbon, silica gel and the like are suitably used. When purified using activated carbon, it is preferable that the compound (I) be adsorbed on activated carbon, washed sufficiently with water, then, eluted by ca. 20% water-containing lower alcohol to obtain an elution fraction which is then recovered. On the other hand, when purified using silica gel, it is preferable that the compound (I) be adsorbed on activated carbon, then, an elution fraction is obtained while appropriately lowering hydrophobicity of elution liquid, to recover the compound (I). The compound (I) is developed with chloroform:methanol:water (70:30:4) using silica gel thin layer chromatography, an anisaldehyde sulfate reagent is sprayed, and the compound (I) is heated. In this procedure, it can be recognized by a spot of dark blue color at an Rf of about 0.6. For this reason, it is simplest to purify the compound (I) using such a detection method.

The compound (I) of this embodiment manifests an obesity ameliorating action, a lipid metabolism ameliorating action, a hypoglycemic action and a hair growth ameliorating action.

The obesity ameliorating agent of this embodiment contains the compound (I) as an active ingredient, and manifests obesity ameliorating actions such as a body weight decreasing action (action of suppressing increase in body weight), a body fat decreasing action (action of suppressing increase in body fat) and the like. The lipid metabolism ameliorating agent of this embodiment contains the compound (I) as an active ingredient, and manifests lipid metabolism ameliorating actions such as a serum cholesterol concentration lowering action, a serum triglyceride concentration lowering action and the like. The hypoglycemic agent of this embodiment contains the compound (I) as an active ingredient, and manifests a hypoglycemic action. The hair growth ameliorating agent of this embodiment contains the compound (I) as an active ingredient, and manifests a hair growth ameliorating action.

All of the obesity ameliorating agent, the lipid metabolism ameliorating agent, the hypoglycemic agent and the hair growth ameliorating agent are produced by subjecting the compound (I) to a known preparation method, for example, by mixing the compound (I) with a pharmaceutically acceptable carrier. It is preferable that all of the obesity ameliorating agent, the lipid metabolism ameliorating agent and the hypoglycemic agent are administered orally, and it is preferable that the hair growth ameliorating agent is administered transdermally. Examples of the dosage form when administered orally are not particularly restricted and include a tablet, granules, powder, fine particles, a capsule, a soft capsule and syrup. Examples of the dosage form when administered transdermally are not particularly restricted and include lotion.

In the case of the dosage form such as a tablet, granules, powder, fine particles and the like, the compound (I) is mixed into a usual medical additive, then, made into a drug formulation according to an ordinary method. Examples of the pharmaceutically acceptable carriers include disintegrating agents such as lactose, starch, crystalline cellulose, silicic anhydride, synthetic aluminum silicate and the like, excipients such as carboxymethylcellulose calcium, sodium alginate and the like, lubricants such as magnesium stearate, talc and the like, and binders such as hydroxypropylcellulose, polyvinylpyrrolidone and the like. In the case of the capsule, the above-mentioned granule, fine particle, powder or the like is filled appropriately in a capsule, to provide a drug formulation. In the case of the soft capsule, the compound (I) is dissolved or suspended in a lipid excipient such as vegetable oil, oily emulsion, glycol and the like, to provide a drug formulation. In the case of the syrup, the compound (I) is dissolved or suspended in an aqueous solution containing saccharose, carboxymethylcellulose and the like, to provide a drug formulation.

When the compound (I) of this embodiments is orally administered, usually, it is preferable that the dosage of 0.1 to 100 mg/kg per day per adult is administered, once a day or 2 to 3 times separately a day, though varying depending on the condition (pathology of patient), age, diathesis and the like of a person to which the compound is administered. When the hair growth ameliorating agent of this embodiments is transdermally administered, usually, it is preferable that the dosage of the compound (I) of 0.1 to 100 mg/kg per day per adult is applied on an affected area, once a day or 2 to 3 times separately a day, though varying depending on the condition (pathology of patient), age, diathesis and the like of a person to which the compound is administered.

When the dosage per day of the compound (I) is less than 0.1 mg/kg, a sufficient pharmacological action cannot be manifested, and in contrast, when the dosage is over 100 mg/kg, an economical demerit is generated though a sufficient pharmacological action can be manifested. The compound (I) did not provide a recognizable side effect even if administered at a dosage of 2500 mg/kg per day.

The effect to be manifested depending on the embodiment is described below.

The compound (I) of this embodiment is 1-O-β-D-glucopyranosylgeraniol-10,5-olide represented by the formula (1). The compound (I) is a novel compound available from natural products, more specifically, originated from crude drugs, and additionally, has various pharmacological actions such as an obesity ameliorating action, a lipid metabolism ameliorating action, a hypoglycemic action, a hair growth ameliorating action and the like. Therefore, the compound (I) can be utilized as an active ingredient of an obesity ameliorating agent, a lipid metabolism ameliorating agent, a hypoglycemic agent, a hair growth ameliorating agent and the like, and thus is extremely useful.

Each of the obesity ameliorating agent, the lipid metabolism ameliorating agent, the hypoglycemic agent and the hair growth ameliorating agent of this embodiment contain the compound (I) as an active ingredient, therefore, they can manifest an obesity ameliorating action, a lipid metabolism ameliorating action, a hypoglycemic action and a hair growth ameliorating action, respectively. Accordingly, all of the obesity ameliorating agent, the lipid metabolism ameliorating agent, the hypoglycemic agent and the hair growth ameliorating agent can be used in applications such as medicine, healthy foods and the like.

Examples of the present invention are described. The present invention is not limited to these examples. In the examples, mice were used. The results obtained in the examples can be applied to any of mammals including humans.

Isolation and Determination of Structure of Compound (I)

25.5 kg of dried branches of S. angustata were pulverized and extracted with water, to obtain an aqueous extract. This aqueous extract was dried to obtain 3.0 kg of dried extract. Subsequently, this dried extract was further extracted under reflux with heating with 3 L of ethanol three times, to obtain 1.39 kg of an ethanol extract.

The compound (I) in the ethanol extract is developed with chloroform:methanol:water (70:30:4) using silica gel thin layer chromatography (Merck, silica gel F254.5554), an anisaldehyde sulfate reagent is sprayed, and the compound (I) is heated. In this procedure, its spot of dark blue color is recognized at around Rf=0.6. Separation described below was carried out using this spot as an index.

1 kg of the ethanol extract was applied on a column (120× 800 mm) filled with 1 kg of activated carbon (Wako Pure Chemical Industries, Ltd., Lot No. PKM0399), and the column was washed until the eluted substance disappeared approximately completely using purified water as the eluent. A solute of about 160 g was eluted by purified water. Then, elution was performed using 20% ethanol to confirm a dark blue spot around Rf=0.6 due to an anisaldehyde sulfate reagent. Elution was continued until this spot was not recognized, to obtain 98 g of a solute as a 20% ethanol fraction.

Next, this 20% ethanol fraction was subjected to a silica gel column (manufactured by Merck, silica gel 60, for column chromatography, 60×450 mm), and eluted using ethyl acetate as an eluent. All of the eluents from initiation of elution with ethyl acetate from the column until no detection were collected separately using a dark blue spot of the compound (I) by an anisaldehyde sulfate reagent as an index, to find that the solutes contained in the fractions were all approximately the compound (I). The structure of the compound (I) was determined based on the measurement results in FIGS. 1 to 7. It was confirmed that the compound (I) was a novel compound and was 1-O-β-D-glucopyranosylgeraniol-10,5-olide represented by the formula (1).

Investigation of Obesity Ameliorating Action, Lipid Metabolism Ameliorating Action and Hypoglycemic Action 6 week-old ddY male SPF mice (Nippon .SLC, body weight: about 30 g) were pre-bred for 1 week, then, divided into two groups of a control group and an administration group (5 mice for each group). Each of the mice in both the groups was bred for 6 weeks with a high fat diet (lard 40%, corn starch 10%, granulated sugar 9%, mineral mix 4%, vitamin mix 1%, casein 29%, cellulose 5%, lactose 2%). For the mice in the administration group, a specimen solution prepared by dissolving the compound (I) in purified water was continuously administered for 6 weeks with a dose of 250 mg/kg once a day while allowing water-drinking, and the body weight was measured at a frequency of once a week, during the feeding period with the high fat diet. For the mice in the control group, purified water was administered for 6 weeks instead of the specimen solution while allowing water-drinking.

The average value of the body weight of mice in each group and the standard error thereof were measured, and a significant difference test (t-test) between both the groups was carried out. The results are shown in FIG. 8.

Figure 8:
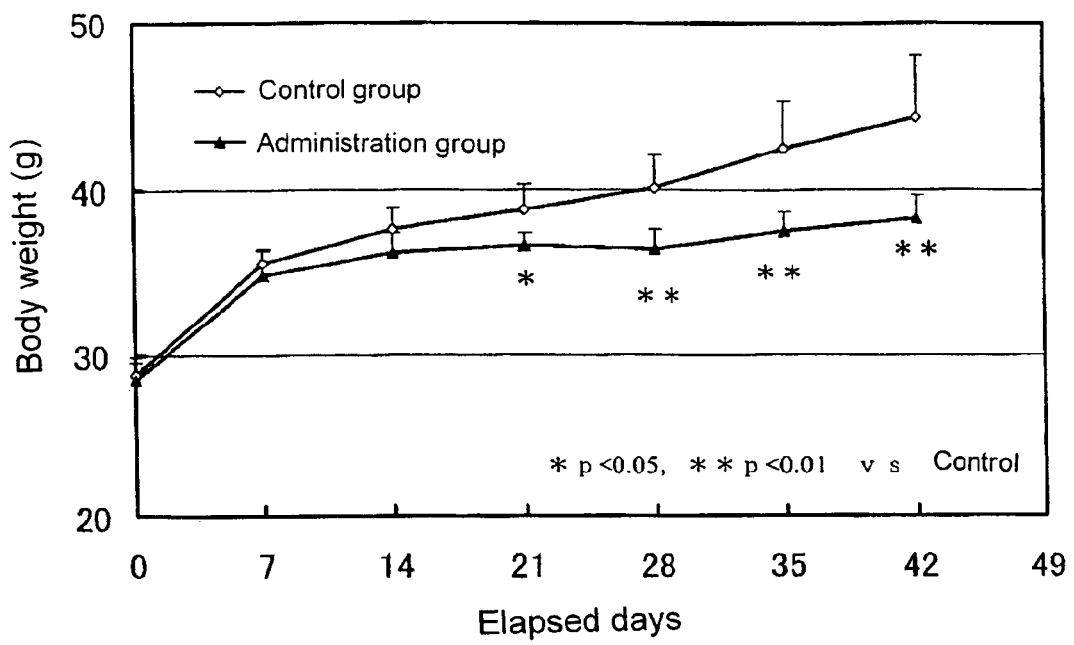
FIG. 8 is a graph showing an obesity ameliorating action of an example.

As shown in FIG. 8, mice in the control group which took the high fat diet showed a steep increase in body weight. By referring to the results of the previous test for mice bred with a usual diet (high carbohydrate diet), an apparent induction of obesity in the mice in the control group was confirmed. In contrast, in the mice in the administration group to which the compound (I) was administered simultaneously, the body weight transited at a lower level, and a statistically significant difference was confirmed as compared with the control group. That is, it was shown that the compound (I) has an action of suppressing an increase in body weight. When the mice in the control group and the mice in the administration group were compared, the diet taking amount and the water taking amount were approximately the same during the administration period allowing water-drinking.

On the other hand, after completion of the above-mentioned continuous administration allowing water-drinking for 6 weeks, serum was collected from each mouse and blood biochemical values were measured, and liver and fat were excised and the weights of them were measured, respectively. Using the respective measurement results, the average value and the standard error were measured for each group, and a significant difference test (t-test) was carried out between both the groups. The results are shown in Table 1.

TABLE 1

| Group | Weight of liver (g) | Weight of fat (g) | | |
| --- | --- | --- | --- | --- |
| | | Around kidney | Around posterior abdominal wall | Around epididymis |
| Control group | 1.400 +/− 0.215 | 0.116 +/− 0.113 | 0.291 +/− 0.120 | 1.540 +/− 0.559 |
| Administration group | 1.124 +/− 0.124 | 0.035 +/− 0.010 | 0.186 +/− 0.096 | 0.445** +/− 0.215 |

| Group | Blood biochemical value (mg/dL) | | |
| --- | --- | --- | --- |
| | Total cholesterol | Triglyceride | Blood glucose level |
| Control group | 161 +/− 30.4 | 94 +/− 21.7 | 228 +/− 19.5 |
| Administration group | 118 +/− 22.3 | 26 +/− 15.8 | 183 +/− 35.7** |

In both groups, average value ± standard error of five mice is shown.
**$p < 0.05$,
$p < 0.01$ vs control group As shown in Table 1, liver weights, fat around the kidney and fat around the posterior abdominal wall were compared, respectively, to find a tendency that the value in the administration group was lower than the value in the control group. Regarding the weight of fat around the epididymis, the value in the administration group was significantly lower than the value in the control group. That is, it was shown that the compound (I) had an action of lowering body fat, particularly, viscus fat or an action of suppressing an increase in fat. Thus, the results in FIG. 8** and Table 1 showed that the compound (I) had an action of ameliorating obesity.

Further, as apparent from Table 1, the administration group showed a significantly lower value than the control group regarding the serum total cholesterol concentration and the serum triglyceride concentration. That is, it was shown that the compound (I) had an action of ameliorating lipid metabolism. Also, as apparent from the Table 1, the administration group showed a significantly lower value than the control group regarding the blood glucose level. That is, it was shown that the compound (I) had an action of lowering blood glucose. When the compound (I) was dissolved in purified water and orally administered for two weeks at a dose of 2500 mg/kg per day to ten 6 week-old ICR male mice (body weight: about 30 g), no side effect was recognized at all as compared with the control group in which the compound (I) was not administered.

Investigation of Hair Growth Ameliorating Action 6 week-old C3H male mice (Nippon SLC, body weight: about 30 g) were pre-bred for 1 week, then, divided into two groups of a control group and an administration group (4 mice for each group). Hair on the back of the mice in both groups was removed with an electric shaver, and hair growth effect was investigated. For each of the mice in the administration group, a specimen solution prepared by dissolving the compound (I) in 45% water-containing ethanol was administered transdermally for 28 days so as to spread this in the form of a square 2 cm×2 cm on skin at the back of the hair-removed mouse at an application amount of 0.1 mL (10 mg in terms of weight of compound (I)) once a day, and hair growth condition were observed at a frequency of once a day. For the mice in the control group, 45% water-containing ethanol was transdermally administered instead of the specimen solution for 28 days.

For observation of hair growth condition, hair growth score and hair length were measured.

For measurement of hair growth score, the back of a mouse on which a specimen solution or 45% water-containing ethanol had been applied was visually observed, and based on the conditions directly after hair removal, a case of no change was endowed with 0 point, a case of color change to blue at a center portion on the back was endowed with 1 point, a case of color change from blue black to gray at a center portion on the back was endowed with 2 points, a case of observation of hair growth at a center portion on the back was endowed with 3 points, and a case of covering about 50% at a center portion on the back with back hair and recovery of color before hair removal at a center portion on the back was endowed with 4 points. The score average value and the standard error of the mice in both the groups were measured. Since there was observed little irregularity in hair growth score between the control group and the administration group, the Mann-Whitney U-test was carried out as a significant difference test between both groups. Part of these results are shown in FIG. 9.

Figure 9:
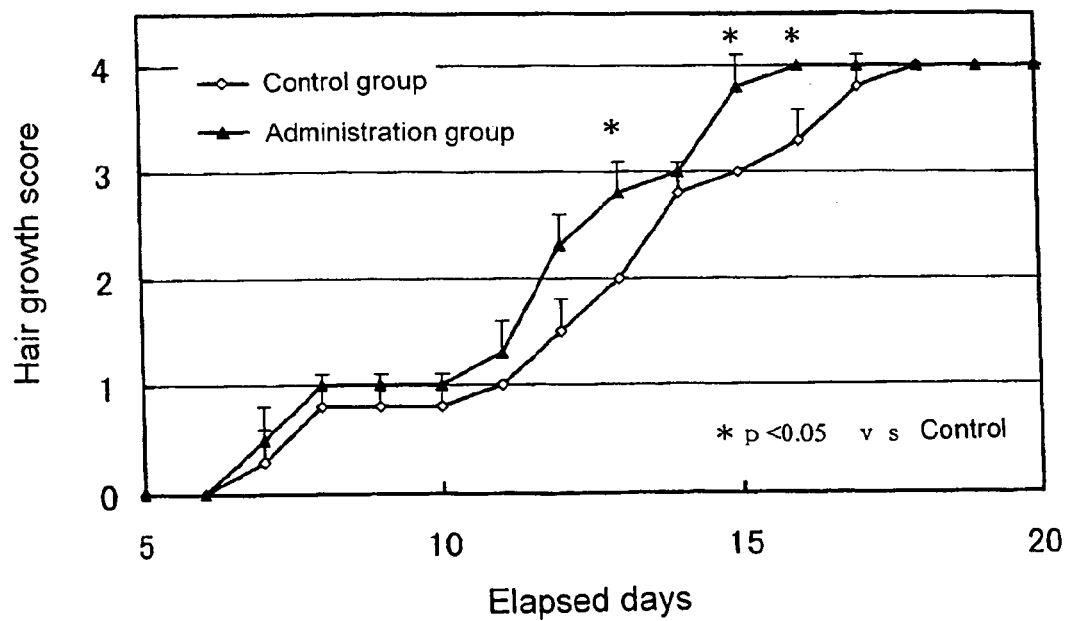
FIG. 9 is a graph showing a hair growth ameliorating action of an example.

As shown in FIG. 9, a change was observed at the back of a mouse from day 7 after transdermal administration, and back hair of all mice recovered color before hair removal at day 18, in the respective groups. Here, between day 7 to day 17 after transdermal administration, the hair growth score in the administration group tended to be higher than that in the control group, in the respective groups, and at days 13, 15 and 16 after transdermal administration, the hair growth score in the administration group was significantly higher than that in the control group, in the respective groups. Thus, the hair growth initiation period in the administration group was approximately the same as in the control group, while there was observed a tendency for growing of hair after recognition of hair growth, namely, a tendency of promoting hair growth.

On the other hand, for measurement of hair length, part of hair was collected every one week, then, 10 hairs were selected randomly while removing extremely longer hairs and extremely shorter hairs, and lengths of them were measured by a microscope. As a result, there was observed no significant difference between the administration group and the control group, though data is not shown, and the hair length in the administration group after initiation of hair growth tended to be always longer than the hair length in the control group. That is, it was shown that the compound (I) had an action of ameliorating hair growth.

FORMULATION EXAMPLE 1

Fine Particle 4.10 parts by weight of the compound (I), 0.14 parts by weight of lactose, 1.30 parts by weight of corn starch, 0.37 parts by weight of silicic anhydride and 0.09 parts by weight of magnesium stearate were sufficiently mixed. This mixture was made into a plate with a compression molding agent, then, ground by an oscillator into granules. Finally, the granules were classified, to obtain fine particles containing 683 mg of the compound (I) in 1 g.

FORMULATION EXAMPLE 2

Tablet 3.00 parts by weight of the compound (I), 1.00 part by weight of lactose, 0.50 parts by weight of corn starch, 0.20 parts by weight of synthetic aluminum silicate, 0.25 parts by weight of carboxymethylcellulose calcium and 0.05 parts by weight of magnesium stearate were sufficiently mixed. This mixture was tabletted so that 300 mg was contained per one tablet, to obtain a tablet containing 180 mg of the compound (I) in one tablet.

FORMULATION EXAMPLE 3

Capsule 3.34 parts by weight of the compound (I), 0.18 parts by weight of synthetic aluminum silicate and 0.18 parts by weight of magnesium stearate were sufficiently mixed. 370 mg of this mixture was filled into a capsule, to obtain a capsule containing 334 mg of the compound (I) in one capsule.

It should be apparent to those skilled in the art that the present invention may be embodied in many other specific forms without departing from the spirit or scope of the invention. Particularly, it should be understood that the present invention may be embodied in the following forms.

The hair growth ameliorating agent may also be utilized as medicated cosmetics such as shampoo, rinse and the like.

The compound (I) may be contained in foods such as bread, cake, munch and the like, dairy products such as milk, yogurt and the like, and beverages such as soft drinks and the like.

The compound (I) may be administered to domestic animals such as horses, cows and pigs (non-human mammals), poultry such as a chickens and the like, or pets such as dogs, cats and the like, in addition to humans.

It is possible to produce a hair growth ameliorating agent containing an extract of leaves of *S. angustata* as an active, ingredient. Examples of the extract include aqueous extracts, lower alcohol extracts, water-containing lower alcohol extracts, and purified extracts obtained by purifying these extracts by activated carbon, silica gel and the like. These extracts contain the compound (I), therefore, a hair growth ameliorating action can be manifested. A hair growth ameliorating agent containing the extract as an active ingredient can be used as a raw material for medicine, medicated cosmetics and healthy foods.

An obesity ameliorating agent and a hypoglycemic agent containing the extract as an active ingredient may be produced. An obesity ameliorating agent, a hypoglycemic agent and a hair growth ameliorating agent containing the ground substance of leaves of *S. angustata* may be produced.

The present examples and embodiments are to be considered as illustrative and not restrictive, and the invention is not to be limited to the details given herein, but may be modified within the scope and equivalence of the appended claims.

What is claimed is:

1. An isolated compound according to formula (1)

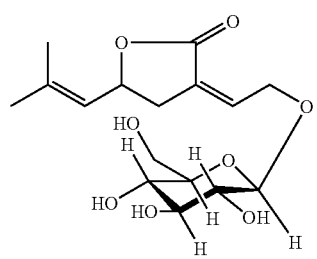

2. The compound according to claim 1, which is isolated from leaves of *S. angustata*.

3. An obesity ameliorating agent comprising an isolated compound according to formula (1):

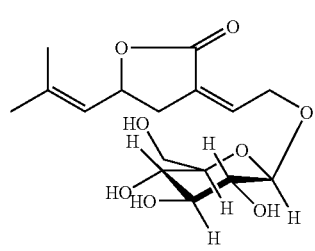

as an active ingredient.

4. A lipid metabolism ameliorating agent comprising an isolated compound according to formula (1):

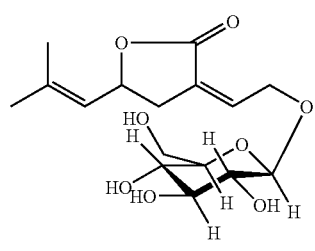

as an active ingredient.

5. A hypoglycemic agent comprising an isolated compound according to formula (1):

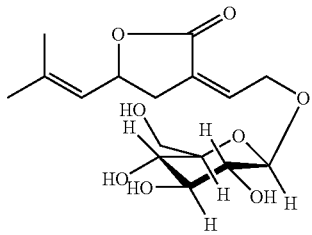

(1)

as an active ingredient.

6. A hair growth ameliorating agent comprising an isolated compound according to formula (1):

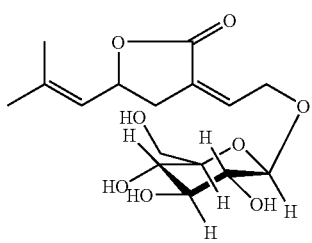

(1)

as an active ingredient.

7. A healthy food comprising an isolated compound according to formula (1):

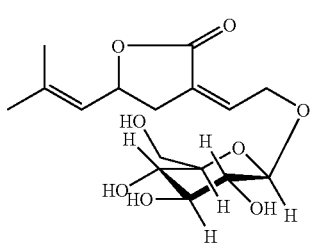

(1)

as an active ingredient.

8. A food comprising an isolated compound according to formula (1):

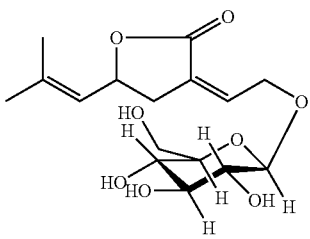

(1)

as an active ingredient.

9. A method for producing a drug formulation, comprising:

extracting leaves of *S. angustata* with a solvent;

isolating from the extract a compound of formula (1) as follows;

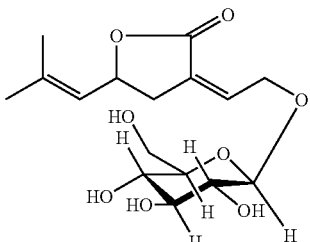

(1)

purifying the compound (1); and mixing a therapeutically effective amount of the isolated compound (1) with a pharmaceutically acceptable carrier.

* * * * *